(12) United States Patent
Yokoyama et al.

(10) Patent No.: US 9,164,386 B2
(45) Date of Patent: Oct. 20, 2015

(54) NEGATIVE-WORKING PHOTOSENSITIVE SILOXANE COMPOSITION

(71) Applicant: AZ ELECTRONIC MATERIALS (LUXEMBOURG) S.A.R.L., Somerville, NJ (US)

(72) Inventors: Daishi Yokoyama, Shizuoka (JP); Atsuko Noya, Shizuoka (JP); Yuji Tashiro, Shizuoka (JP); Naofumi Yoshida, Shizuoka (JP); Yasuaki Tanaka, Shizuoka (JP); Takashi Fuke, Shizuoka (JP); Megumi Takahashi, Shizuoka (JP); Katsuto Taniguchi, Shizuoka (JP); Toshiaki Nonaka, Shizuoka (JP)

(73) Assignee: AZ ELECTRONIC MATERIALS (LUXEMBOURG) S.A.R.L., Luxembourg (LU)

( * ) Notice: Subject to any disclaimer, the term of this patent is extended or adjusted under 35 U.S.C. 154(b) by 0 days.

(21) Appl. No.: 14/388,187

(22) PCT Filed: Apr. 5, 2013

(86) PCT No.: PCT/JP2013/060519
§ 371 (c)(1),
(2) Date: Sep. 25, 2014

(87) PCT Pub. No.: WO2013/151167
PCT Pub. Date: Oct. 10, 2013

(65) Prior Publication Data
US 2015/0064613 A1   Mar. 5, 2015

(30) Foreign Application Priority Data
Apr. 6, 2012 (JP) ................... 2012-087257

(51) Int. Cl.
*G03F 7/004* (2006.01)
*G03F 7/075* (2006.01)
*G03F 7/085* (2006.01)
*C07F 7/18* (2006.01)
*C08L 83/04* (2006.01)
*C09D 183/04* (2006.01)
*C09D 183/06* (2006.01)
*G03F 7/30* (2006.01)

(52) U.S. Cl.
CPC ............ *G03F 7/0757* (2013.01); *C07F 7/1804* (2013.01); *C07F 7/1836* (2013.01); *C08L 83/04* (2013.01); *C09D 183/04* (2013.01); *C09D 183/06* (2013.01); *G03F 7/0755* (2013.01); *G03F 7/085* (2013.01); *G03F 7/30* (2013.01)

(58) Field of Classification Search
CPC ..... G03F 7/027; G03F 7/0755; G03F 7/0757; G03F 7/085; C07F 7/1804; C07F 7/1836; C08L 83/04; C09D 183/04; C09D 183/06; C09D 5/00

USPC ............... 430/270.1, 3, 322, 330, 331, 272.1
See application file for complete search history.

(56) References Cited

U.S. PATENT DOCUMENTS

| | | | |
|---|---|---|---|
| 8,809,482 B2 * | 8/2014 | Fu et al. ......................... | 528/43 |
| 2006/0192481 A1 | 8/2006 | Nagayama et al. | |
| 2006/0286484 A1 | 12/2006 | Powell et al. | |
| 2007/0134916 A1 * | 6/2007 | Iwabuchi et al. ............. | 438/636 |
| 2007/0218402 A1 * | 9/2007 | Kinsho et al. ............... | 430/270.1 |
| 2010/0273110 A1 * | 10/2010 | Ogihara et al. ............... | 430/324 |
| 2011/0008589 A1 * | 1/2011 | Kimura et al. ............. | 428/195.1 |
| 2013/0210229 A1 * | 8/2013 | Ogihara et al. ............... | 438/694 |
| 2013/0210236 A1 * | 8/2013 | Ogihara et al. ............... | 438/706 |
| 2013/0284699 A1 * | 10/2013 | Ogihara et al. ................. | 216/48 |

FOREIGN PATENT DOCUMENTS

| | | |
|---|---|---|
| JP | 2933879 B2 | 5/1999 |
| JP | 2004-10697 A | 1/2004 |
| JP | 2006-236839 A | 9/2006 |
| JP | 2007-187721 A | 7/2007 |
| JP | 2008-546204 A | 12/2008 |
| JP | 2010-8603 A | 1/2010 |
| JP | 2010-39051 A | 2/2010 |
| JP | 2010-39053 A | 2/2010 |
| JP | 2010-39056 A | 2/2010 |
| JP | 2010-151946 A | 7/2010 |
| JP | 2010-152302 A | 7/2010 |
| JP | 2011-95432 A | 5/2011 |
| JP | 2011-190333 A | 9/2011 |
| SG | 184100 A1 | 10/2012 |

(Continued)

OTHER PUBLICATIONS

Machine translation of JP 2010-039051 (no date).*
Machine translation of WO 2011/114995 (no date).*

(Continued)

*Primary Examiner* — Amanda C Walke
(74) *Attorney, Agent, or Firm* — Mitchell Brustein

(57) ABSTRACT

[Object]
To provide a negative-working photosensitive siloxane composition developable inorganically, and also to provide a cured film-manufacturing method employing that.

[Means]
The present invention provides a negative-working photosensitive siloxane composition comprising a polysiloxane, a silicon-containing compound having a pKa of 2.0 to 15.7, a photo-polymerization initiator, and a solvent. This composition is coat on a substrate, exposed to light, developed with an inorganic developer, and heated, so that a cured film can be obtained.

12 Claims, No Drawings

(56) References Cited

FOREIGN PATENT DOCUMENTS

| WO | WO 2006/073021 A1 | 7/2006 |
|----|-------------------|--------|
| WO | WO 2011/114995 B1 | 9/2011 |

OTHER PUBLICATIONS

Eng. Trans. of the International Preliminary Report on Patentability (Form PCT/IPEA/409) mail date May 7, 2013 for PCT/JP2013/060519, which corresponds to U.S. Appl. No. 14/388,187.

Morrison & Boyd, Organic Chemistry 4th Edition, Section 19.10-Section 19.15, pp. 789-pp. 797 (1983).

Machine Language English Abstract from Espacenet and Translation from JPO of JP 5422872 B2 A1, which is equivalent to WO 2006/073021 A1.

Jean-Ho Song et al., "Views on the low-resistant bus materials and their process architecture for the large-sized & post-ultra definition TFT-LCD", IMID/IDMC/Asia Display 2008 Digest, pp. 9-pp. 12.

* cited by examiner

NEGATIVE-WORKING PHOTOSENSITIVE SILOXANE COMPOSITION

This application is a United States National Stage Patent Application under 35 U.S.C. §371 of International Patent Application No. PCT/JP2013/060519, filed Apr. 5, 2013, which claims priority to Japanese Patent Application No. 2012-087257, filed Apr. 6, 2012, the contents of which are being hereby incorporated herein by reference.

TECHNICAL FIELD

The present invention relates to a negative-working photosensitive siloxane composition. Further, this invention also relates to a cured film-manufacturing method employing the composition, a cured film formed from the composition, and a device comprising the cured film.

BACKGROUND ART

In the field of optical devices, such as, displays, light emitting diodes and solar cells, various proposals have been recently made for the purposes of energy conservation and of improvement in light utilization efficiency. For example, there is a known method for increasing the aperture ratio of a liquid crystal display. In that method, a transparent planarization film is formed to cover a thin-film transistor (hereinafter, often referred to as "TFT") element and then pixel electrodes are formed on the planarization film (see, Patent document 1). Similarly to this method for a liquid crystal display, there is also a method proposed in order to increase the aperture ratio of an organic electric field light-emitting device (hereinafter, often referred to as "organic EL device"). In the proposed method, the constitution of the device is changed from a type in which a light-emitting layer is formed by deposition on transparent pixel electrodes provided on a substrate so that the emitted light is extracted from the substrate side (i.e., bottom emission type) to another type in which a TFT element, a planarization film formed thereon to cover the TFT element, transparent pixel electrodes provided thereon, and a light-emitting layer formed thereon are so laminated that the light given off from the light-emitting layer is extracted from the side opposite to the TFT element (i.e., top emission type) (see, Patent document 2).

According as new technologies such as 3D displaying have been introduced to meet increasing needs for improvement of displays in resolution, in upsizing and in image quality, signal delay on the wiring has been becoming a problem. Specifically, the speed of rewriting image information (i.e., frame frequency) has been accelerated, and accordingly the input time of signals into the TFT element has been shortened. However, even if it is attempted to improve the response speed by broadening the wiring width to reduce the wiring resistance, the broadening of the wiring width is limited by the requirements of high resolution displaying and the like. In view of that, it is proposed to increase the wiring thickness so as to solve the problem of signal delay (see, Non-patent document 1).

As one of the materials for the planarization film formed on a TFT substrate, it is known to adopt a negative-working photosensitive material mainly comprising a polysiloxane compound and a polymerization initiator. The polysiloxane compound is obtained by polymerization of a bifunctional group-containing silane compound, such as, dialkyldialkoxysilane, in the presence of catalysis. However, the conventional siloxane-containing negative-working photosensitive material has a problem to be improved. Specifically, when developed with an inorganic developer, a coating of the material intended to be removed by the developer may still remain after the development. Because of that, it has been difficult to develop the coating inorganically although inorganic development has the advantages of being very safe and of making it possible to obtain high contrast as compared with development with an organic developer, such as, tetraammonium hydroxide.

PRIOR ART DOCUMENTS

Patent Documents

[Patent document 1] Japanese Patent No. 2933879
[Patent document 2] Japanese Patent Laid-Open No. 2006-236839
[Patent document 3] Re-publication of PCT International Publication No. 2006-073021
[Patent document 4] Japanese Patent Laid-Open No. 2011-190333

Non-Patent Documents

[Non-patent document 1] IMID/IDMC/ASIA DISPLAY 2008 Digest (pp. 9-pp. 12)

DISCLOSURE OF INVENTION

Problem to be Solved by the Invention

In consideration of the above, it has been desired to provide a negative-working photosensitive siloxane composition which is superior to conventional ones both in sensitivity and in resolution, which forms a cured film better than conventional ones in optical or physical characteristics and which can be developed inorganically.

Means for Solving Problem

The present invention provides a negative-working photosensitive siloxane composition, comprising
a polysiloxane,
a silicon-containing compound having a pKa of 2.0 to 15.7 in water at 25° C.,
a photo-polymerization initiator, and
a solvent.

The present invention also provides a cured film-manufacturing method comprising the steps of: coating on a substrate the above negative-working photosensitive siloxane composition, to form a coating; exposing the coating to light; developing the exposed coating with an inorganic developer; and heating the developed coating.

The present invention further provides a cured film formed from the above negative-working photosensitive siloxane composition.

The present invention furthermore provides a device comprising the above cured film.

Effect of the Invention

The present invention provides a negative-working photosensitive siloxane composition which does not contain an organic group, such as an acrylic group, capable of playing the principal role of polymerization and which can be developed with an inorganic developer, such as, an aqueous solution of sodium hydroxide or potassium hydroxide (hereinafter, that kind of development is often referred to as "inorganic development"). A photosensitive layer formed from this composition has high sensitivity and high resolution, and also has such excellent developability as to leave few residues after development. Further, a cured film formed from the composition is excellent in transparency, in heat resistance, in chemical resistance and in environmental durability. This cured film can achieve excellent characteristics when used in a planarization film provided on a thin-film transistor (TFT) substrate adopted as a backplane of a display, such as, a liquid crystal display or an organic EL display; when used in an interlayer insulating film in a semiconductor element; or when used in an optical device, such as, a solid-state image sensor, an anti-reflective film, an anti-reflective plate, an optical filter, a superluminescent light-emitting diode, a touch panel, a solar cell or an optical waveguide.

BEST MODE FOR CARRYING OUT THE INVENTION

Embodiments of the present invention will be described below in detail.
Negative-Working Photosensitive Siloxane Composition The negative-working photosensitive siloxane composition of the present invention comprises a polysiloxane, a silicon-containing compound, a photo-polymerization initiator and a solvent. The following will explain, in order, the polysiloxane, the silicon-containing compound, the photo-polymerization initiator and the solvent used in the composition of the present invention.
(I) Polysiloxane The composition according to the present invention contains a polysiloxane as a main component. The term "polysiloxane" means a polymer having Si—O—Si bonds, and it means not only an unsubstituted inorganic polysiloxane but also an organic group-substituted organic polysiloxane in the present invention. The polysiloxane compound generally has silanol groups or alkoxysilyl groups. The terms "silanol groups" and "alkoxysilyl groups" mean hydroxyl groups and alkoxy groups, respectively, which directly connect to silicon atoms constituting the siloxane skeleton. Those groups have a function of promoting a curing reaction when a cured film is formed from the composition, and also are thought to contribute to the later-described reaction with the silicon-containing compound. Accordingly, the polysiloxane compound preferably has those groups.

The polysiloxane used in the present invention is not particularly restricted on its structure, and can be freely selected in accordance with the aimed applications. According to the number of oxygen atoms connecting to a silicon atom, the structure of polysiloxane can be generally categorized into the following three skeletons, that is: silicone skeleton (in which two oxygen atoms connect to a silicon atom), silsesquioxane skeleton (in which three oxygen atoms connect to a silicon atom), and silica skeleton (in which four oxygen atoms connect to a silicon atom). In the present invention, the polysiloxane may have any of those skeletons. Further, the structure of the polysiloxane molecular may be a combination of two or more of them.

In the case where an organic polysiloxane is adopted, substituent groups contained therein can be freely selected unless they impair the effect of the present invention. The substituent groups are, for example, groups having no Si—O bonds, which constitute the siloxane structure Examples thereof include alkyl groups, alkenyl groups, hydroxyalkyl groups, and aryl groups.

The siloxane resin may have reactive groups other than the silanol or alkoxysilyl groups, such as, carboxyl groups, sulfonyl groups, and amino groups, unless they impair the effect of the present invention. However, those reactive groups generally tend to lower the storage stability of the composition, and hence they are preferably contained in a small amount. In addition, if the resin contains acidic groups, such as, thiol, phosphonium, borate, carboxyl, phenol, peroxide, nitro, cyano and sulfo groups, those acidic groups remain in the formed coating to deteriorate the characteristics thereof. Accordingly, they are preferably contained in a small amount. Specifically, the amount thereof is preferably 10 mol % or less based on the total number of hydrogen atoms or substituent groups connecting to silicon atoms. Further, it is particularly preferred for the resin not to contain those reactive groups at all.

It is for the purpose of forming a cured film that the composition of the present invention is coat on a substrate, imagewise exposed to light and then developed. This means that there must be a difference in solubility between the exposed area and the unexposed area. In the present invention, the exposed area undergoes a curing reaction to be insoluble in a developer and thereby to form an image. Accordingly, the polysiloxane in the unexposed area should be soluble in a developer more than a certain degree. For example, if the formed coating has a dissolution rate of 50 Å/second or more in a 2.38% aqueous solution of tetramethylammonium hydroxide (hereinafter often referred to as "TMAH"), it is thought to be possible to produce a negative pattern by exposure-development procedure. However, the polysiloxane must be properly selected according to the development conditions because the required solubility depends on those conditions.

If a polysiloxane having a high dissolution rate is simply selected to use, problems may arise in that the pattern shape may be deformed, in that the area of remaining coating may be decreased and in that the transparency may be reduced. In order to cope with those problems, it is possible to adopt a polysiloxane mixture containing a polysiloxane having a low dissolution rate.

The polysiloxane mixture, for example, comprises
(Ia) a first polysiloxane the coating of which after prebaked is soluble in a 5 wt % aqueous solution of tetramethylammonium hydroxide at a dissolution rate of 3000 Å/second or less, and
(Ib) another polysiloxane the coating of which after prebaked has a dissolution rate of 150 Å/second or more in a 2.38 wt % aqueous solution of tetramethylammonium hydroxide.
Those polysiloxane compounds will be explained below.
(a) First Polysiloxane The coating of the first polysiloxane (Ia) after prebaked is soluble in a 5 wt % aqueous solution of tetramethylammonium hydroxide, and the dissolution rate thereof is 3000 Å/second or less, preferably 2000 Å/second or less. This polysiloxane by itself is slightly soluble in a 2.38% TMAH aqueous solution.

The first polysiloxane can be produced by hydrolyzing in the presence of basic catalysis and condensing a silane compound (ia) selected from the group consisting of trialkoxysilanes and tetraalkoxysilanes.

The silane compound (ia) as a starting material may be any one selected from the group consisting of trialkoxysilanes and tetraalkoxysilanes. For example, it can be represented by the following formula (i):

$$R^1{}_n Si(OR^2)_{4-n} \qquad \text{(i)}$$

in which $R^1$ is a straight, branched or cyclic alkyl group of 1 to 20 carbon atoms in which any methylene may be replaced with oxygen or otherwise is an aryl group of 6 to 20 carbon atoms in which any hydrogen may be replaced with fluorine; n is 0 or 1; and $R^2$ is an alkyl group of 1 to 5 carbon atoms.

Examples of $R^1$ in the formula (i) include methyl, ethyl, n-propyl, iso-propyl, t-butyl, n-hexyl, n-decyl, trifluoromethyl, 2,2,2-trifluoroethyl, 3,3,3-trifluoropropyl, cyclohexyl, phenyl, tollyl and naphthyl groups. The compound having a methyl group as $R^1$ is particularly preferred because that material is easily available and the resultant cured film has sufficient hardness and high chemical resistance. Also preferred is a phenyl group because it enhances solubility of the polysiloxane in the solvent and makes the resultant cured film hardly suffer from cracking.

Examples of $R^2$ in the formula (i) include methyl, ethyl, n-propyl, iso-propyl, and n-butyl groups. The formula (I) has two or more $R^2$s, which may be the same or different from each other.

Concrete examples of the trialkoxysilane compounds represented by the formula (i) include methyltrimethoxysilane, methyltriethoxysilane, methyltriiso-propoxysilane, methyltri-n-butoxysilane, ethyltri-methoxysilane, ethyltriethoxysilane, ethyltriiso-propoxysilane, ethyltri-n-butoxysilane, n-propyltrimethoxysilane, n-propyltriethoxysilane, n-butyltri-methoxysilane, n-butyltriethoxysilane, n-hexyltri-methoxysilane, n-hexyltriethoxysilane, decyltrimethoxy-silane, phenyltrimethoxysilane, phenyltriethoxysilane, naphthyltri-methoxysilane, naphthyltriethoxysilane, naphthyltriisopropoxysilane, naphthyltri-n-butoxysilane, trifluoromethyltrimethoxysilane, trifluoromethyltri-ethoxysilane, and 3,3,3-trifluoropropyltrimethoxysilane. Among them, preferred are methyltrimethoxysilane, methyltriethoxysilane, phenyltrimethoxysilane and phenyltriethoxysilane because they are easily available.

Further, concrete examples of the tetraalkoxysilane compounds represented by the formula (i) include tetramethoxysilane, tetraethoxysilane, tetrapropoxy-silane, and tetrabutoxysilane. Among them, preferred are tetramethoxysilane and tetraethoxysilane because they have high reactivity.

For synthesis of the first polysiloxane (Ia), the silane compound (ia) may be used singly or in combination of two or more. If tetraalkoxysilanes are adopted as the silane compound (Ia), they tend to reduce heat collapsing of the pattern. This is thought to be because the crosslinking density increases in the polysiloxane. However, if tetraalkoxysilanes are used too much, the sensitivity may be lowered. In view of that, if tetraalkoxysilanes are employed as a material of the polysiloxane (Ia), the amount thereof is preferably 0.1 to 40 mol %, more preferably 1 to 20 mol %, based on the total molar amount of the trialkoxysilane and tetraalkoxysilane compounds.

The polysiloxane (Ia) used in the present invention is preferably produced by hydrolyzing in the presence of basic catalysis and condensing the above silane compound.

For example, it can be produced by the steps of: dropping the silane compound or a mixture thereof into a reaction solvent comprising an organic solvent, basic catalysis and water, so as to conduct hydrolysis and condensation reactions; purifying by neutralizing or by washing or condensing the reaction solution, if necessary; and replacing the reaction solvent with a desired organic solvent, if necessary.

Examples of the organic solvent adoptable as the reaction solvent include: hydrocarbons, such as, hexane, toluene, xylene and benzene; ethers, such as, diethyl ether and tetrahydrofuran; esters, such as, ethyl acetate and propylene glycol monomethylethylacetate; alcohols, such as, methanol, ethanol, iso-propanol, butanol and 1,3-dipropanol; and ketones, such as, acetone, methyl ethyl ketone and methyl isobutyl ketone. Those organic solvents can be employed singly or in combination. The amount of the organic solvent is generally 0.1 to 10 times by weight, preferably 0.5 to 2 times the weight of the mixture of the silane compound.

The temperature at which the hydrolysis and condensation reactions are conducted is generally 0 to 200° C., preferably 10 to 60° C. The temperature of the dropped silane compound may be the same as or different from that of the reaction solvent. The reaction time depends on the kind of the silane compound and the like, but is normally several tens of minutes to several tens of hours, preferably 30 minutes or more. Various conditions of the hydrolysis and condensation reactions, such as, the amount of the basic catalysis, the reaction temperature and the reaction time, are properly selected in consideration of the reaction scale and the size and shape of the reaction vessel, so as to obtain characteristics suitable for the aimed use.

Examples of the basic catalysis include: organic bases, such as, triethylamine, tripropylamine, tributylamine, tripentylamine, trihexylamine, triheptylamine, trioctylamine, diethylamine, triethanolamine, diethanolamine, and alkoxysilane having amino group; inorganic bases, such as, sodium hydroxide and potassium hydroxide; and tertiary ammonium salts, such as, anion exchange resin, tetrabutylammonium hydroxide, tetraethylammonium hydroxide, and tetramethylammonium hydroxide. The amount of the catalysis is preferably 0.0001 to 10 times the mole of the mixture of the silane compound. The polysiloxane synthesized by use of the basic catalysis is characterized in that it rapidly begins to cure when heated at 150° C. or more and in that the pattern thereof can keep the shape clearly even after cured without suffering from heat collapsing.

The degree of the hydrolysis can be controlled by how much water is added to the reaction solvent. It is generally preferred to make hydrolytic alkoxy groups in the silane compound react with water in an amount of 0.01 to 10 times by mole, preferably 0.1 to 5 times the mole of the groups. If the added amount of water is smaller than the above, the hydrolysis degree is too low to form a coating of the composition. That is unfavorable. On the other hand, however, if it is too much, the composition easily undergoes gelation and hence has low storage stability. That is unfavorable, too. The water is preferably ion exchange water or distilled water.

After the reactions are completed, the reaction solution may be made neutral or weakly acidic by use of an acidic compound as a neutralizer. Examples of the acidic compound include: inorganic acids, such as, phosphoric acid, nitric acid, sulfuric acid, hydrochloric acid and hydrofluoric acid; and organic acids, such as, acetic acid, trifluoroacetic acid, formic acid, lactic acid, acrylic acid, multivalent carboxylic acids (e.g., oxalic acid, maleic acid, succinic acid, citric acid) and anhydrides thereof, and sulfonic acids (e.g., p-toluenesulfonic acid and methanesulfonic acid). Further, cation exchange resin can be used as a neutralizer.

The amount of the neutralizer is properly selected according to pH of the reaction solution after the reactions, but is preferably 0.5 to 1.5 times by mole, more preferably 1 to 1.1 times the mole of the basic catalysis. In the case where cation exchange resin is adopted, the number of ionic groups in the exchange resin is preferably in the above range.

According to necessity, the reaction solution after neutralized can be washed and purified. There are no particular restrictions on the way of washing. For example, hydrophobic organic solvent and water, if necessary, are added to the reaction solution after neutralized, and then the mixture was stirred and thereby the organic solvent is brought into contact with the polysiloxane so as to dissolve at least the polysiloxane (Ia) in the hydrophobic organic solvent phase. As the hydrophobic organic solvent, a compound capable of dissolving the polysiloxane (Ia) but immiscible with water is employed. Here, the compound "immiscible with water" means that, even if water and the compound are well mixed, the mixture separates into an aqueous phase and an organic phase while left to stand.

Preferred examples of the hydrophobic organic solvent include: ethers, such as, diethyl ether; esters, such as, ethyl acetate; alcohols having low solubility in water, such as, butanol; ketones, such as, methyl ethyl ketone and methyl isobutyl ketone; and aromatic solvents, such as, toluene and xylene. The hydrophobic organic solvent used in washing may be the same as or different from the organic solvent used as the reaction solvent, and further two or more solvents may be mixed to use. In this washing step, most of the basic catalysis used in the reactions, the neutralizer, salts formed by the neutralization, and by-products of the reactions, such as, alcohols and water, are contained in the aqueous phase and hence essentially removed from the organic phase. The times of washing can be changed according to necessity.

The temperature in washing is not particularly restricted, but is preferably 0 to 70° C., more preferably 10 to 60° C. The temperature at which the aqueous phase and the organic phase are separated is also not particularly restricted, but is preferably 0 to 70° C., more preferably 10 to 60° C. in view of shorting the time for separating the phases.

The above washing step may improve the composition in coatability and in storage stability.

The reaction solution after washed may be directly added to the composition of the present invention, but can be condensed, if necessary, to remove the solvent and remaining by-products, such as, alcohols and water, and thereby to change the concentration. Further, the solvent may be replaced with another solvent. The solution can be condensed under normal (atmospheric) pressure or reduced pressure, and the degree of condensation can be freely changed by controlling the distilled amount. The temperature in the condensation step is generally 30 to 150° C., preferably 40 to 100° C. According to the aimed solvent composition, a desired solvent may be added and then the solution may be further condensed to replace the solvent.

In the above manner, the polysiloxane (Ia) usable in the siloxane resin composition of the present invention can be produced.

(b) Second Polysiloxane

The coating of the second polysiloxane after prebaked is soluble in a 2.38 wt % aqueous solution of tetramethylammonium hydroxide, and the dissolution rate thereof is 150 Å/second or more, preferably 500 Å/second or more.

This polysiloxane (Ib) can be produced by hydrolyzing in the presence of acidic or basic catalysis and condensing a silane compound (ib) selected from the group consisting of trialkoxysilanes and tetraalkoxysilanes.

The conditions of the above production process may be the same as those for the polysiloxane (Ia). However, acidic catalysis as well as basic catalysis can be employed as the reaction catalysis. In order to realize the aimed dissolution rate, the conditions, such as, the reaction solvent, particularly, the amount of added water, the reaction time, and the reaction temperature, are properly controlled.

The silane compound (ib) may be the same as or different from the silane compound (ia), which is used as a material of the polysiloxane (Ia). If tetraalkoxysilanes are adopted as the silane compound (ib), they tend to reduce heat collapsing of the pattern.

If a relatively large amount of tetraalkoxysilane is used as a material of the first polysiloxane (Ia), it is preferred to use a small amount of tetraalkoxysilane as a material of the second polysiloxane (Ib). That is because, if containing a large amount of tetraalkoxysilane in total, the formed coating often suffers from deposition of the silane compound or from deterioration of sensitivity. Accordingly, the amount of tetraalkoxysilane is preferably 1 to 40 mol %, more preferably 1 to 20 mol %, based on the total molar amount of the silane compounds (ia) and (ib), which are materials of the polysiloxanes (Ia) and (Ib), respectively.

In producing the polysiloxane (Ib), acidic catalysis can be used as the reaction catalysis. Examples of the acidic catalysis include hydrochloric acid, nitric acid, sulfuric acid, hydrofluoric acid, phosphoric acid, acetic acid, trifluoroacetic acid, formic acid, and multivalent carboxylic acids and anhydrides thereof. The amount of the catalysis depends on the strength of the acid, but is preferably 0.0001 to 10 times the mole of the mixture of the silane compound.

In the case where the acidic catalysis is adopted to produce the polysiloxane (Ib), the reaction solution may be neutralized after the reactions are completed in the same manner as in the case where the basic catalysis is adopted. In this case, basic compounds are employed as the neutralizer. Examples of the basic compounds used for neutralization include: organic bases, such as, triethylamine, tripropylamine, tributylamine, tripentylamine, trihexylamine, triheptylamine, trioctylamine, diethylamine, triethanolamine, and diethanolamine; inorganic bases, such as, sodium hydroxide and potassium hydroxide; and tertiary ammonium salts, such as, tetrabutylammonium hydroxide, tetraethylammonium hydroxide, and tetramethylammonium hydroxide. In addition, anion exchange resin is also employable. The amount of the neutralizer may be the same as that in the case where the basic catalysis is adopted. Specifically, that is properly selected according to pH of the reaction solution after the reactions, but is preferably 0.5 to 1.5 times by mole, more preferably 1 to 1.1 times the mole of the acidic catalysis.

In the above manner, the polysiloxane (Ib) usable in the siloxane resin composition of the present invention can be produced.

As described later, the polysiloxane (Ib) has a rate of dissolution in a 2.38 wt % TMAH aqueous solution necessarily in the range of 150 Å/second or more, preferably in the range of 500 Å/second or more. If the polysiloxane (Ib) has a dissolution rate of less than 150 Å/second in a 2.38 wt % TMAH aqueous solution, it is necessary to reduce the amount of the polysiloxane (Ia), which is slightly soluble, as much as possible in order that the mixture of the polysiloxanes (Ia) and (Ib) can have a rate of dissolution in a 2.38 wt % TMAH aqueous solution in the range of 50 to 3000 Å/second. However, if the polysiloxane (Ia) is contained in a small amount, it is difficult to prevent heat collapsing of the pattern.

(c) Polysiloxane Mixture (I)

In the present invention, a polysiloxane mixture (I) containing the above polysiloxanes (Ia) and (Ib) can be used. There are no particular restrictions on the mixing ratio of the polysiloxanes (Ia) and (Ib), but the weight ratio of the polysiloxanes (Ia)/(Ib) is preferably 1/99 to 80/20, more preferably 20/80 to 50/50 in the polysiloxane mixture (I).

If the polysiloxane (Ia) has a dissolution rate of 3000 Å/second or less in a 5 wt % TMAH aqueous solution and also if the polysiloxane (Ib) has a dissolution rate of 150 Å/second or more in a 2.38 wt % TMAH aqueous solution, serious problems of insufficient dissolution and of sensitivity deterioration can be avoided. However, it is possible to properly select the dissolution rate of the polysiloxane mixture (I) in a 2.38 wt % TMAH aqueous solution according to the thickness and developing time of the cured film formed from the negative-working photosensitive siloxane composition of the present invention. The dissolution rate of the polysiloxane mixture (I) can be controlled by changing the mixing ratio of the polysiloxanes (Ia) and (Ib). Although depending on the kind and amount of the photosensitive material contained in the negative-working photosensitive siloxane composition, the dissolution rate of the polysiloxane mixture (I) is, for example, preferably 50 to 3000 Å/second in a 2.38 wt % TMAH aqueous solution provided that the film has a thickness of 0.1 to 10 μm (1000 to 100000 Å).

(d) Alkali Dissolution Rate in TMAH Aqueous Solution

In the present invention, the polysiloxanes (Ia) and (Ib) individually have specific dissolution rates in TMAH aqueous solutions. The dissolution rate of polysiloxane in a TMAH aqueous solution is measured in the following manner. First, the polysiloxane is diluted with propyleneglycol monomethyletheracetate (hereinafter, referred to as "PGMEA") to be 35 wt %, and stirred and dissolved with a stirrer for 1 hour at room temperature. In a clean-room under an atmosphere of temperature: 23.0±0.5° C. and humidity: 50±5.0%, the prepared polysiloxane solution is then dropped with a pipet in an amount of 1 cc onto a 4-inch silicon wafer of 525 μm thickness at the center area, and spin-coated to form a coating of 2±0.1 μm thickness. Thereafter, the coating is pre-baked for 90 seconds on a hot-plate at 100° C. to remove the solvent. The thickness of the coating is then measured with a spectro-ellipsometer (manufactured by J. A. Woollam).

Subsequently, the silicon wafer covered with the coating is placed in a 6 cm-diameter glass petri dish filled with 100 ml of a TMAH aqueous solution of predetermined concentration at 23.0±0.1° C., and left to be immersed. The time it takes for the coating to disappear is measured, and the dissolution rate is obtained by dividing the thickness by the time it takes for the solution to dissolve and remove the coating in the area from the wafer edge to 10-nm inside. Otherwise, in the case where the dissolution rate is extremely slow, the wafer is immersed in the TMAH aqueous solution for a predetermined time and then heated for 5 minutes on a hot-plate at 200° C. to remove water soaking in the coating during the measurement of dissolution rate, and thereafter the thickness of the coating is measured. The thickness change between before and after the immersion is divided by the immersing time to obtain the dissolution rate. The above measurement is repeated five times and the obtained values are averaged to determine the dissolution rate of the polysiloxane.

As described above, either a single polysiloxane or a polysiloxane mixture can be used in the present invention. In either case, the weight average molecular weight (Mw) of the polysiloxane or polysiloxane mixture is preferably 5000 or less, more preferably 1000 to 4000. If the weight average molecular weight is less than 1000, it is difficult to avoid heat collapsing of the pattern. On the other hand, if it is more than 5000, the coating is so insufficiently dissolved away in the development step that satisfying resolution cannot be obtained and also that the sensitivity may be lowered. Here, the "weight average molecular weight" means a polystyrene-reduced weight average molecular weight determined by gel permission chromatography (GPC).

(II) Silicon-Containing Compound

The composition of the present invention contains a silicon-containing compound. The silicon-containing compound used in the present invention has a pKa in a particular range. The "pKa" in the present invention means a pKa in water at 25° C. unless otherwise noted. Specifically, the silicon-containing compound used in the present invention has a pKa of necessarily 15.7 or less, preferably 10 or less. That is because, the lower pKa, namely, the higher acidity the composition has, the less the coating thereof is not removed to remain after development, in other words, the more the developability is improved. On the other hand, the silicon-containing compound has a pKa of necessarily 2.0 or more, preferably 3.0 or more. That is because, if the silicon-containing compound has too high a pKa, the composition easily undergoes gelation and hence has low stability. In order to realize a pKa in the above range, the silicon-containing compound has a proper acidic group or an acidic group protected with a protective group capable of being readily eliminated by external stimulation, such as, acid, base, heat or the like.

If having a pKa smaller than silanol groups, the silicon-containing compound tends to improve developability. Although depending on the structure, the pKa of silanol groups is generally 7 to 10. Accordingly, the silicon-containing compound particularly preferably has a pKa of 7 or less. It is not clear why the effect of the present invention appears remarkably if the pKa is as small as the above, but it is presumed that the reaction between the silicon-containing compound and silanol groups in the polysiloxane is promoted to improve the solubility of the polysiloxane in a developer.

Here, the pKa of the silicon-containing compound can be experimentally obtained according to the titration method or the absorptiometric method, or can be calculated on the basis of the results thereof. The pKa values thus obtained are set forth in, for example, Evans pKa Table (Evans Group, Harvard University).

The reason why the silicon-containing compound is used in the present invention is that it has high compatibility with the polysiloxane in the composition. Actually, even if a compound having a pKa satisfying the above condition but not containing silicon is adopted, the effect of the present invention cannot be obtained. This is thought to be because the expected reaction does not proceed sufficiently if the compound has poor compatibility with the polysiloxane in the composition. The silicon-containing compound contains silicon preferably in the form of a silyl group, a siloxane bond or a silazane bond.

Examples of the silicon-containing compound are acidic group-containing silane or siloxane compounds. Examples of the acidic group include carboxyl group, an acid anhydride group, and phenolic hydroxyl group. If having a monobasic acid group such as carboxyl or phenolic hydroxyl group, the compound is preferably a single silicon-containing compound having two or more acidic groups.

Examples of the silicon-containing compound preferably used in the present invention include compounds represented by the following formula (A):

$$X_nSi(OR^3)_{4-n} \qquad (A)$$

and polymers having polymerization units derived from them. Those polymers may comprise plural kinds of units different in X or $R^3$ in combination.

In the above formula, $R^3$ is a hydrocarbon group, such as, an alkyl group. Examples thereof include methyl, ethyl, n-propyl, iso-propyl and n-butyl groups. The formula (A) contains plural $R^3$s, which may be the same or different from each other.

In the above formula, X includes an acidic group, such as, thiol, phosphonium, borate, carboxyl, phenol, peroxide, nitro, cyano, sulfo or alcohol group. The acidic group may be protected with a protective group, such as, acetyl, aryl, amyl, benzyl, methoxymethyl, mesyl, tollyl, trimethoxysilyl, triethoxysilyl, triisopropylsilyl or trityl group. Further, X may be an acid anhydride group.

Among the above, $R^3$ and X are preferably methyl group and a carboxylic acid anhydride group, respectively. For example, an acid anhydride group-containing silicone is preferred. Concrete examples thereof are a compound represented by the following formula (A-1) (X-12-967C [trademark], manufactured by Shin-Etsu Chemical Co., Ltd.) and a silicon-containing polymer, such as silicone, having a structure corresponding the formula at the terminal or in the side chain and having a weight average molecular weight of 1000 or less. Also preferred is a dimethyl silicone having a weight average molecular weight of 4000 or less and having a terminal modified with an acidic group, such as, thiol, phosphonium, borate, carboxyl, phenol, peroxide, nitro, cyano or sulfo group. Examples thereof include compounds represented by the following formulas (A-2) and (A-3) (X-22-2290AS and X-22-1821 [trademark], manufactured by Shin-Etsu Chemical Co., Ltd.).

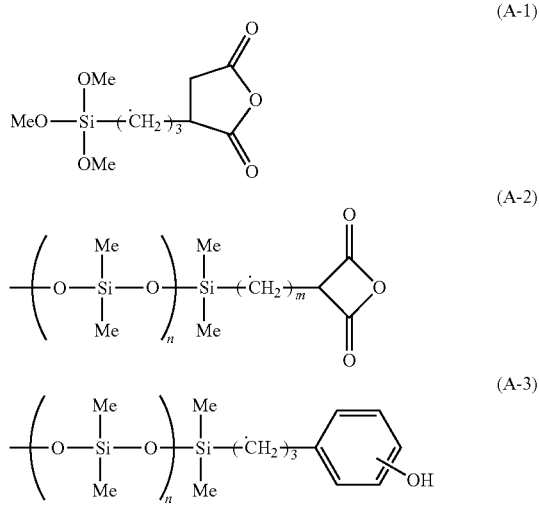

If the silicon-containing compound contains a silicone structure and has too large a molecular weight, it has poor compatibility with the polysiloxane in the composition. Consequently, the coating is dissolved in a developer so insufficiently that reactive groups remains in the coating. This may cause problems in that, for example, the coating cannot have enough chemical resistance against post-processes. In view of that, the silicon-containing compound has a weight average molecular weight of preferably 5000 or less, more preferably 1000 to 4000.

In the present invention, the amount of the silicon-containing compound can be freely designed according to the aimed application. However, if the silicon-containing compound is used in an increased amount in the present invention, the developability with an inorganic developer is improved. Accordingly, the amount of the silicon-containing compound is preferably 0.5 weight part or more, further preferably 1.0 weight part or more based on 100 weight parts of the polysiloxane. On the other hand, however, if the silicon-containing compound is added too much, the coating even in an unexposed area may be removed in development to lower resolution and contrast of the pattern. In view of that, the amount of the silicon-containing compound is preferably 8M weight parts or less, further preferably 5.0 weight parts or less based on 100 weight parts of the polysiloxane.

As described above, the silicon-containing compound may be a polymer. However, if having too large a molecular weight, the compound often has such poor solubility that reactive groups may remain in the formed coating. As a result, this may cause problems in that, for example, the coating cannot have enough chemical resistance against post-processes. In view of that, the silicon-containing compound has a weight average molecular weight of preferably 1000 or less.

(iii) Photo-Polymerization Initiator

The negative-working photosensitive siloxane composition of the present invention contains a photo-polymerization initiator. There are two kinds of polymerization initiators: one is a photo-polymerization initiator, which generates an acid or based when exposed to radiation; and the other is a heat polymerization initiator, which generates an acid or based when exposed to heat.

The polymerization initiator can reinforce the pattern shape or can increase contrast in development to improve the resolution. The polymerization initiator adoptable in the present is, for example, a photo acid-generator, which decomposes when exposed to radiation and releases an acid serving as an active substance for photo-curing the composition; a photo base-generator, which releases a base; a heat acid-generator, which decomposes when exposed to heat and releases an acid serving as an active substance for heat-curing the composition; and a heat base-generator, which releases a base. Examples of the radiation include visible light, UV rays, IR rays, X-rays, electron beams, α-rays and γ-rays. The above polymerization initiators are different in whether light or heat is necessary to generate an acid or a base. In the present invention, the composition necessarily comprises a photo-polymerization initiator, but may also comprise a heat polymerization initiator in combination so as to promote the polymerization reaction by heating.

The amount of the polymerization initiator depends on the kind of the active substance released from the decomposed initiator, on the amount of the released substance, on the required sensitivity and on the dissolution contrast between the exposed and unexposed areas. However, it is preferably 0.001 to 10 weight parts, more preferably 0.01 to 5 weight parts, based on 100 weight parts of the polysiloxane. If the amount is less than 0.001 weight part, the dissolution contrast between the exposed and unexposed areas may be too low to obtain the effect of the initiator. On the other hand, if it is more than 10 weight parts, the formed film may suffer from cracks or may be colored by decomposition of the initiator so seriously that the colorless transparency of the coating may be impaired. Further, if the polymerization initiator is contained too much, the decomposed initiator may lower the electric insulation of the cured film or may release gases to cause troubles in the post-processes. Furthermore, it often deteriorates resistance of the coating against a photoresist remover containing monoethanolamine or the like as a main component.

Examples of the above photo acid-generator include diazomethane compounds, diphenyliodonium salts, triphenylsulfonium salts, sulfonium salts, ammonium salts, phosphonium salts and sulfonamide compounds. The structures of those photo acid-generators can be represented by the formula (A):

$$R^+X^- \qquad (A).$$

In the above formula, $R^+$ is hydrogen or an organic ion modified by carbon atoms or other hetero atoms provided that the organic ion is selected from the group consisting of alkyl groups, aryl groups, alkenyl groups, acyl groups and alkoxy groups. For example, $R^+$ is diphenyliodonium ion or triphenylsulfonium ion.

Further, $X^-$ is preferably a counter ion represented by any of the following formulas:

$SbY_6^-$, $AsY_6^-$, $R^a_p PY_{6-p}^-$, $R^a_q BY_{4-q}^-$, $R^a_q GaY_{4-q}^-$, $R^a SO_3^-$, $(R^a SO_2)_3 C^-$, $(R^a SO_2)_2 N^-$, $R^a COO^-$, and $SCN^-$ in which
Y is a halogen atom,
$R^a$ is an alkyl group of 1 to 20 carbon atoms or an aryl group of 6 to 20 carbon atoms provided that each group is substituted with a substituent group selected from the group consisting of fluorine, nitro group and cyano group,
$R^b$ is hydrogen or an alkyl group of 1 to 8 carbon atoms,
P is a number of 0 to 6, and
q is a number of 0 to 4.

Concrete examples of the counter ion include: $BF_4^-$, $(C_6F_5)_4B^-$, $((CF_3)_2C_6H_3)_4B^-$, $PF_6^-$, $(CF_3CF_2)_3PF_3^-$, $SbF_6^-$, $AsF_6^-$, $(C_6F_5)_4Ga^-$, $((CF_3)_2C_6H_3)_4Ga^-$, $SCN^-$, $(CF_3SO_2)_3C^-$, $(CF_3SO_2)_2N^-$, formate ion, acetate ion, trifluoromethanesulfonate ion, nonafluorobutanesulfonate ion, methane-sulfonate ion, butanesulfonate ion, benzenesulfonate ion, p-toluenesulfonate ion, and sulfonate ion.

Among the photo acid-generators usable in the present invention, those generating sulfonic acids or boric acids are particularly preferred. Examples thereof include tricumyliodonium teterakis(pentafluorophenyl)-borate (PHOTOINITIATOR2074 [trademark], manufactured by Rhodorsil), diphenyliodonium tetra(perfluorophenyl)borate, and a compound having sulfonium ion and pentafluoroborate ion as the cation and anion moieties, respectively. Further, examples of the photo acid-generators also include triphenylsulfonium trifluoromethanesulfonate, triphenylsulfonium camphorsulfonate, triphenylsulfonium tetra(perfluorophenyl)-borate, 4-acetoxyphenyldimethylsulfonium hexafluoroarsenate, 1-(4-n-butoxynaphthalene-1-yl)tetrahydrothiophenium trifluoromethanesulfonate, 1-(4,7-dibutoxy-1-naphthalenyl)tetrahydrothiophenium trifluoromethanesulfonate, diphenyliodonium trifluoromethanesulfonate, and diphenyliodonium hexafluoroarsenate. Furthermore, it is still also possible to adopt photo acid-generators represented by the following formulas:

in which
each A is independently a substituent group selected from the group consisting of an alkyl group of 1 to 20 carbon atoms, an alkoxy group of 1 to 20 carbon atoms, an aryl group of 6 to 20 carbon atoms, an alkylcarbonyl group of 1 to 20 carbon atoms, an arylcarbonyl group of 6 to 20 carbon atoms, hydroxyl group, and amino group; each p is independently an integer of 0 to 5; and
$B^-$ is a fluorinated alkylsulfonate group, a fluorinated arylsulfonate group, a fluorinated alkylborate group, an alkylsulfonate group or an arylsulfonate group.

It is also possible to use photo acid-generators in which the cations and anions in the above formulas are exchanged each other or combined with various other cations and anions described above. For example, any one of the sulfonium ions represented by the above formulas can be combined with tetra(perfluorophenyl)-borate ion, and also any one of the iodonium ions represented by the above formulas can be combined with tetra(perfluorophenyl)borate ion. Those can be still also employed as the photo acid-generators.

The above heat acid-generator is, for example, a salt or ester capable of generating an organic acid. Examples thereof include: various aliphatic sulfonic acids and salts thereof; various aliphatic carboxylic acids, such as, citric acid, acetic acid and maleic acid, and salts thereof; various aromatic carboxylic acids, such as, benzoic acid and phthalic acid, and salts thereof; aromatic sulfonic acids and ammonium salts thereof; various amine salts; aromatic diazonium salts; and phosphonic acid and salts thereof. Among the heat acid-generators usable in the present invention, salts of organic acids and organic bases are preferred, and further preferred are salts of sulfonic acids and organic bases.

Examples of the preferred heat acid-generators containing sulfonate ions include p-toluenesulfonates, benzenesulfonates, p-dodecylbenzenesulfonates, 1,4-naphthalene-disulfonates, and methanesulfonates. Those heat acid-generators can be used singly or in mixture.

Examples of the above photo base-generator include multi-substituted amide compounds having amide groups, lactams, imide compounds, and compounds having those structures.

Examples of the above heat base-generator include: imidazole derivatives, such as, N-(2-nitro-benzyloxycarbonyl)imidazole, N-(3-nitrobenzyloxycarbonyl)imidazole, N-(4-nitrobenzyloxycarbonyl)imidazole, N-(5-methyl-2-nitrobenzyloxycarbonyl)imidazole, and N-(4-chloro-2-nitrobenzyloxycarbonyl)imidazole; 1,8-diazabicyclo(5,4,0)undecene-7, tertiary amines, quaternary ammonium salts, and mixture thereof. Those base-generators as well as the acid-generators can be used singly or in mixture.

(IV) Solvents

The negative-working photosensitive siloxane composition of the present invention contains a solvent. There are no particular restrictions on the solvent as long as it can homogeneously dissolve or disperse the above polysiloxane, the polymerization initiator, and additives incorporated optionally. Examples of the solvent usable in the present invention include: ethylene glycol mono-alkyl ethers, such as, ethylene glycol monomethyl ether, ethylene glycol monoethyl ether, ethylene glycol monopropyl ether, and ethylene glycol monobutyl ether; diethylene glycol dialkyl ethers, such as, diethylene glycol dimethyl ether, diethylene glycol diethyl ether, diethylene glycol dipropyl ether, and diethylene glycol dibutyl ether; ethylene glycol alkyl ether acetates, such as, methyl cellosolve acetate and ethyl cellosolve acetate; propylene glycol alkyl ether acetates, such as, propylene glycol monomethyl ether acetate (PGMEA), propylene glycol monoethyl ether acetate, and propylene glycol monopropyl ether acetate; aromatic hydrocarbons, such as, benzene, toluene and xylene; ketones, such as, methyl ethyl ketone, acetone, methyl amyl ketone, methyl isobutyl ketone, and cyclohexanone; alcohols, such as, ethanol, propanol, butanol, hexanol, cyclohexanol, ethylene glycol, and glycerin; esters, such as, ethyl 3-ethoxypropionate, methyl 3-methoxypropionate and ethyl lactate; and cyclic asters, such as, γ-butyrolactone. Those solvents are used singly or in combination of two or more, and the amount thereof depends on the coating method and the thickness of the coating.

The amount of the solvent in the negative-working photosensitive siloxane composition can be freely controlled according to the method of coating the composition. For example, if the composition is to be spray-coated, it can contain the solvent in an amount of 90 wt % or more. Further, if a slit-coating method, which is often adopted in coating a large substrate, is to be carried out, the content of the solvent is normally 60 wt % or more, preferably 70 wt % or more. However, the amount of the solvent gives little effect to the characteristics of the negative-working photosensitive siloxane composition according to the present invention.

(V) Additives

The negative-working photosensitive siloxane composition of the present invention may contain other additives, if necessary. Examples of the additives include developer-dissolution promoter, scum remover, adhesion enhancer, polymerization inhibitor, defoaming agent, surfactant and sensitizer.

The developer-dissolution promoter or the scum remover has a function of controlling solubility of the formed coating in a developer and thereby of preventing scum from remaining on the substrate after development. As this additive, crown ethers can be adopted. Crown ethers having the simplest structures are represented by the general formula: $(-CH_2-CH_2-O-)_n$. Among them, crown ethers of the formula in which n is 4 to 7 are preferably used in the present invention. Meanwhile, crown ethers are often individually referred to as "x-crown-y-ether" in which x and y represent the total number of atoms forming the ring and the number of oxygen atoms included therein, respectively. In the present invention, the additive is preferably selected from the group consisting of crown ethers of X=12, 15, 18 and 21 and y=x/3, benzo-condensed products thereof, and cyclohexyl-condensed products thereof. Preferred examples of the crown ethers include 21-crown-7-ether, 18-crown-6-ether, 15-crown-5-ether, 12-crown-4-ether, dibenzo-21-crown-7-ether, dibenzo-18-crown-6-ether, dibenzo-15-crown-5-ether, dibenzo-12-crown-4-ether, dicyclohexyl-21-crown-7-ether, dicyclohexyl-18-crown-6-ether, dicyclohexyl-15-crown-5-ether, and dicyclohexyl-12-crown-4-ether. Among them, it is particularly preferred to select the additive from the group consisting of 18-crown-6-ether and 15-crown-5-ether. The amount thereof is preferably 0.05 to 15 weight parts, more preferably 0.1 to 10 weight parts, based on 100 weight parts of the polysiloxane.

The adhesion enhancer has a function of preventing the pattern from being peeled off by stress applied after curing when a cured film is formed from the negative-working photosensitive siloxane composition of the present invention. As the adhesion enhancer, imidazoles and silane coupling agents are preferably adopted. Examples of the imidazoles include 2-hydroxybenzimidazole, 2-hydroxyethylbenzimidazole, benzimidazole, 2-hydroxyimidazole, imidazole, 2-mercaptoimidazole, and 2-aminoimidazole. Among them, particularly preferred are 2-hydroxybenzimidazole, benzimidazole, 2-hydroxyimidazole and imidazole.

As the silane coupling agents, known compounds, such as, epoxy-silane coupling agents, amino-silane coupling agents and mercapto-silane coupling agents, can be preferably adopted. Examples thereof include 3-glycidoxypropyltrimethoxysilane, 3-glycidoxypropyl-triethoxysilane, N-2-(aminoethyl)-3-aminopropyltrimethoxysilane, N-2-(aminoethyl)-3-aminopropyltriethoxysilane, 3-aminopropyltrimethoxysilane, 3-aminopropyltriethoxysilane, 3-ureidopropyltrimethoxy-silane, 3-chloropropyltrimethoxysilane, 3-mercapto-propyltrimethoxysilane, and 3-isocyanatepropyl-trimethoxysilane. Those can be used singly or in combination of two or more. The amount thereof is preferably 0.05 to 15 weight parts based on 100 weight parts of the polysiloxane.

As the polymerization inhibitor, nitrone derivatives, nitroxide radical derivatives and hydroquinone derivatives, such as, hydroquinone, methylhydroquinone and butyllhydroquinine, can be incorporated. Those can be used singly or in combination of two or more. The amount thereof is preferably 0.1 to 10 weight parts based on 100 weight parts of the polysiloxane.

Examples of the defoaming agent include: alcohols ($C_1$ to $C_{18}$); higher fatty acids, such as, oleic acid and stearic acid; higher fatty acid esters, such as, glycerin monolaurate; polyethers, such as, polyethylenglycol (PEG) (Mn: 200 to 10000) and polypropyleneglycol (Mn: 200 to 10000); silicone compounds, such as, dimethyl silicone oil, alkyl-modified silicone oil and fluoro-silicone oil; and organic siloxane surfactants described below in detail. Those can be used singly or in combination of two or more. The amount thereof is preferably 0.1 to 3 weight parts based on 100 weight parts of the polysiloxane.

If necessary, the negative-working photosensitive siloxane composition of the present invention can further contain a surfactant, which is incorporated with the aim of improving coatability, developability and the like. The surfactants usable in the present invention are, for example, nonionic, anionic and amphoteric surfactants.

Examples of the nonionic surfactants include: polyoxyethylene alkyl ethers, such as, polyoxyethylene lauryl ether, polyoxyethylene oleyl ether and polyoxyethylene cetyl ether; polyoxyethylene fatty acid diethers; polyoxyethylene fatty acid monoethers; polyoxyethylene-polyoxypropylene block polymer; acetylene alcohol; acetylene glycol derivatives, such as, acetylene glycol, polyethoxyate of acetylene alcohol, and polyethoxyate of acetylene glycol; silicon-containing surfactants, such as, Fluorad ([trademark], manufactured by Sumitomo 3M Limited), MEGAFAC ([trademark], manufactured by DIC Corporation), and Surufuron ([trademark], manufactured by Asahi Glass Co., Ltd.); and organic siloxane surfactants, such as, KP341 ([trademark], manufactured by Shin-Etsu Chemical Co., Ltd.). Examples of the above acetylene glycols include: 3-methyl-1-butyne-3-ol, 3-methyl-1-pentyne-3-ol, 3,6-dimethyl-4-octyne-3,6-diol, 2,4,7,9-tetra methyl-5-decyne-4,7-diol, 3,5-dimethyl-1-hexyne-3-ol, 2,5-dimethyl-3-hexyne-2,5-diol, and 2,5-dimethyl-2,5-hexanediol.

Examples of the anionic surfactants include: ammonium salts and organic amine salts of alkyldiphenylether disulfonic acids, ammonium salts and organic amine salts of alkyldiphenylether sulfonic acids, ammonium salts and organic amine salts of alkyl-benzenesulfonic acids, ammonium salts and organic amine salts of polyoxyethylenealkylether sulfuric acids, and ammonium salts and organic amine salts of alkyl-sulfuric acids.

Further, examples of the amphoteric surfactants include 2-alkyl-N-carboxymethyl-N-hydroxyethyl imidazolium betaine, and laurylic acid amidopropyl hydroxy sulfone betaine.

Those surfactants can be used singly or in combination of two or more. The amount thereof is normally 50 to 2000 ppm, preferably 100 to 1000 ppm based on the negative-working photosensitive siloxane composition of the present invention.

According to necessity, a sensitizer can be incorporated into the negative-working photosensitive siloxane composition of the present invention. Examples of the sensitizer preferably used in the composition of the present invention include coumarin, ketocoumarin, derivatives thereof, thiopyrylium salts, and acetophenone. Specifically, concrete examples thereof include: sensitizing dyes, such as, p-bis(o-methylstryl)benzene, 7-dimethylamino-4-methyl-quinolone-2,7-amino-4-methylcoumarin, 4,6-dimethyl-7-ethylaminocoumarin, 2-(p-dimethylamino-stryl)pyridylmethyl iodide, 7-diethylaminocoumarin, 7-diethylamino-4-methylcoumarin, 2,3,5,6-1H,4H-tetrahydro-8-methylquinolidino-<9,9a,1-gh>coumarin, 7-diethylamino-4-trifluoromethylcoumarin, 7-dimethylamino-4-trifluoromethylcoumarin, 7-amino-4-trifluoromethylcoumarin, 2,3,5,6-1H,4H-tetrahydroquinolidino-<9,9a,1-gh>coumarin, 7-ethylamino-6-methyl-4-trifluoromethylcoumarin, 7-ethylamino-4-trifluoromethylcoumarin, 2,3,5,6-1H,4H-tetrahydro-9-carboethoxyquinolidino-<9,9a,1-gh>coumarin, 3-(2'-N-methylbenzimidazolyl)-7-N,N-diethylaminocoumarin, N-methyl-4-trifluoromethylpiperidino-<3,2-g>coumarin, 2-(p-dimethylaminostryl)benzothiazolylethyl iodide, 3-(2'-benzimidazolyl)-7-N,N-diethylaminocoumarin, 3-(2'-benzothiazolyl)-7-N,N-diethylaminocoumarin, and pyrylium or thiopyrylium salts represented by the following formula. The sensitizing dye makes it possible to carry out patterning by use of inexpensive light sources, such as, a high-pressure mercury lamp (360 to 430 nm). The amount thereof is preferably 0.05 to 15 weight parts, more preferably 0.1 to 10 weight parts based on 100 weight parts of the polysiloxane.

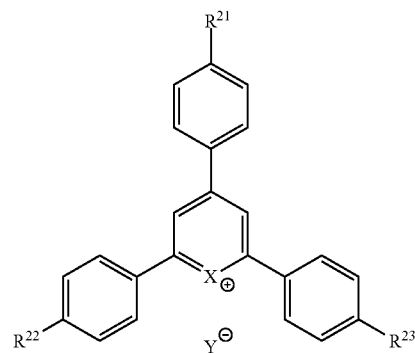

| X | $R_1$ | $R_2$ | $R_3$ | Y |
|---|---|---|---|---|
| S | $OC_4H_9$ | H | H | $BF_4$ |
| S | $OC_4H_9$ | $OCH_3$ | $OCH_3$ | $BF_4$ |
| S | H | $OCH_3$ | $OCH_3$ | $BF_4$ |
| S | $N(CH_3)_2$ | H | H | $ClO_2$ |
| O | $OC_4H_9$ | H | H | $SbF_6$ |

As the sensitizer, it is also possible to adopt a compound having an anthracene skeleton. Concrete examples thereof include compounds represented by the following formula (C):

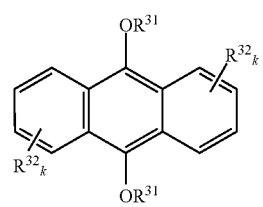

(C)

in which each $R^{31}$ is independently a substituent group selected from the group consisting of alkyl groups, aralkyl groups, aryl groups, hydroxyalkyl groups, alkoxyalkyl groups, glycidyl groups and halogenated alkyl groups;

each $R^{32}$ is independently a substituent group selected from the group consisting of hydrogen, alkyl groups, alkoxy groups, halogen atoms, nitro groups, sulfonic acid groups, hydroxyl group, amino groups, and carboalkoxy groups; and each k is independently an integer of 0 and 1 to 4.

The sensitizers having anthracene skeletons are disclosed in, for example, Patent documents 3 and 4. When the sensitizer having an anthracene skeleton is added, the amount thereof is preferably 0.01 to 5 weight parts based on 100 weight parts of the polysiloxane mixture (I).

Further, if necessary, a stabilizer can be also added into the negative-working photosensitive siloxane composition of the present invention. The stabilizer can be freely selected from those generally known. However, in the present invention, aromatic amines are preferred because they have high effect on stabilization. Among those aromatic amines, preferred are pyridine derivatives and particularly preferred are pyridine derivatives having bulky substituent groups at 2- and 6-positions. Concrete examples thereof are as follows:

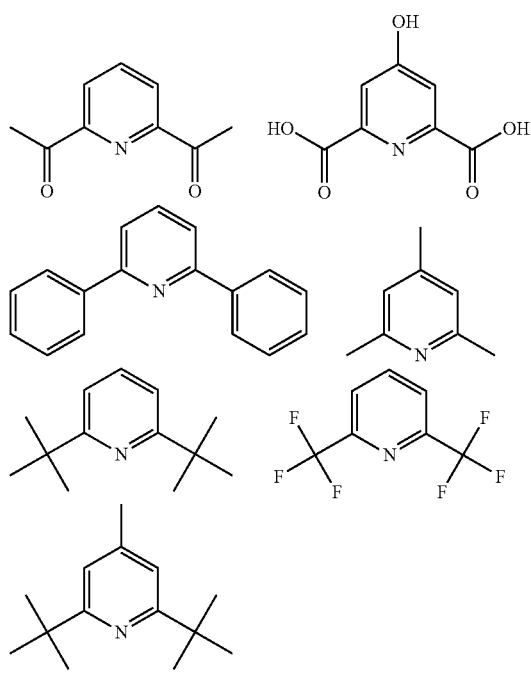

Method for Forming a Cured Film

The cured film-formation method according to the present invention comprises: coating the above negative-working photosensitive siloxane composition on a substrate surface, to form a coating; and heating to cure the coating. The cured film-formation method will be explained below in the order of the steps.

(1) Coating Step

First, the above negative-working photosensitive siloxane composition is coat on a substrate to form a coating. In the present invention, the coating can be formed from the photosensitive siloxane composition in any known manner. Specifically, the coating method can be freely selected from, for example, immersion coating, roll coating, bar coating, brush coating, spray coating, doctor coating, flow coating, spin coating, and slit coating. The substrate to be coated with the composition can be also properly selected from, for example, a silicon substrate, a glass substrate and a resin film. According to necessity, those substrates may be equipped with various semiconductor elements and the like formed thereon. If the substrate is in the form of a film, the coating can be formed by gravure coating. If desired, a drying step can be independently carried out after coating. Further, according to necessity, the coating step may be carried out once or twice or more so as to form a coating of desired thickness.

(2) Prebaking Step

After the negative-working photosensitive siloxane composition is coat to form a coating, the coating is preferably subjected to prebaking (preheating treatment) for the purposes of drying the coating and of reducing the solvent remaining therein. The prebaking step is carried out at a temperature of generally 50 to 150° C., preferably 90 to 120° C. for 10 to 300 seconds, preferably 30 to 120 seconds on a hot-plate or for 1 to 30 minutes in a clean oven.

(3) Exposing Step

After the coating is formed, the surface thereof is exposed to light. As a light source for the exposure, it is possible to adopt any light source used in conventional pattern-formation processes. Examples of the light source include high-pressure mercury lamp, low-pressure mercury lamp, metal halide lamp, xenon lamp, laser diode and LED. Light for the exposure is normally UV rays of g-line, h-line, i-line or the like. Except for in the case of ultrafine fabrication of semiconductors and the like, it is general to use light of 360 to 430 nm (high-pressure mercury lamp) for patterning in several micrometers to several tens of micrometers. Particularly in producing a liquid crystal display, light of 430 nm is often used. As described above, in that case, it is advantageous to combine a sensitizing dye with the negative-working photosensitive siloxane composition of the present invention. Energy of the exposure light depends on the light source and the thickness of the coating, but is generally 10 to 2000 mJ/cm$^2$, preferably 20 to 1000 mJ/cm$^2$. If the exposure energy is lower than 10 mJ/cm$^2$, it is often difficult to obtain satisfying resolution. On the other hand, however, if it is more than 2000 mJ/cm$^2$, the coating is exposed so excessively that the exposure may cause halation.

In order that the coating can be imagewise exposed to light, common photomasks are employable. Any photomask can be selected from known ones. There are no particular restrictions on the environmental conditions in the exposure, and the exposure can be carried out under an ambient atmosphere (the normal atmosphere) or under a nitrogen atmosphere. If a film is to be formed on the whole surface of the substrate, the whole substrate surface is exposed to light. In the present invention, the term "pattern film" includes a film thus formed on the whole surface of the substrate.

(4) Post-Exposure Baking Step

After the exposing step, post-exposure baking is generally carried out according to necessity with the aim of promoting interpolymer reactions caused by the reaction initiator in the exposed area of the coating. This heating treatment is not for the purpose of curing the coating completely but for the purpose of making it possible to leave a desired pattern on the substrate after development and to remove the part other than the pattern by development.

When the post-exposure baking step is carried out, it is possible to use a hot-plate, an oven, a furnace or the like. The heating temperature should not be too high because it is unfavorable for acid generated by exposure in the exposed area to diffuse into the unexposed area. In view of that, the temperature of post-exposure baking is preferably 40 to 150° C., more preferably 60 to 120° C. If necessary, the temperature may be step-by-step increased so as to control the curing speed of the composition. There are no particular restrictions on the atmosphere of baking. In order to control the curing speed of the composition, the atmosphere can be selected from, for example, an atmosphere of inert gas such as nitrogen gas, a vacuum atmosphere, a reduced-pressure atmosphere, an oxygen gas atmosphere and the like. The baking time is preferably longer than a certain period so as to keep higher homogeneity of temperature history in the wafer surface, but also preferably not excessively long so as to prevent the diffusion of acid. In consideration of those, the baking time is preferably 20 to 500 seconds, more preferably 40 to 300 seconds.

(5) Development Step

After the exposing step, the coating is optionally subjected to the post-exposure baking step and thereafter subjected to developing treatment. As a developer used in the development step, it is possible to adopt any developer employed in developing conventional photosensitive siloxane compositions. However, the present invention is characterized by being capable of using an inorganic developer. Development with an inorganic developer is favorable because it has the advantages of being very safe and of making it possible to obtain high contrast as compared with development with an organic developer, such as, tetraammonium hydroxide.

Preferred examples of the developer include aqueous solutions of alkaline inorganic compounds, such as, alkali metal hydroxides (e.g., sodium hydroxide, potassium hydroxide), alkali metal metasilicates (hydrates), and alkali metal phosphates (hydrates). The concentrations of those aqueous solutions are generally, for example, 0.5 to 3.0 wt %. Those may contain water-soluble organic solvents, such as, methanol and ethanol, or surfactants, if necessary.

The developing method can be also freely selected from known methods, such as, dip, paddle, shower, slit, cap coat and spray development processes. As a result of the development, a pattern can be obtained. After developed with a developer, the pattern is preferably washed with water.

In the present invention, development is preferably carried out by use of an inorganic developer. However, it is also possible to use an organic developer, examples of which include aqueous solutions of alkaline organic compounds, such as, tetraalkylammonium hydroxide, choline, ammonia, alkylamines, alkanolamines, and heterocyclic amines.

(6) Heating Step

After the development step, the obtained pattern film is heated and thereby cured. The heating apparatus used in the heating step can be the same as those used in the post-exposure baking step. The heating temperature in this heating step is not particularly restricted as long as the coating can be cured, but is normally 150 to 400° C., preferably 200 to 350° C. If it is lower than 150° C., unreacted silanol groups may remain. The remaining silanol groups may prevent the cured film from having sufficient chemical resistance and also may increase the permittivity of the cured film. In view of that, the heating temperature is preferably 150° C. or more. The heating time is also not particularly restricted, but is generally 10 minutes to 24 hours, preferably 30 minutes to 3 hours. Here, the "heating time" means a period of time from when the temperature of the pattern film is elevated to reach the aimed heating temperature. It normally takes several minutes to several hours to heat the pattern film from the initial temperature up to the aimed heating temperature.

The cured film thus obtained can achieve excellent heat-resistance, transparency and relative permittivity. Specifically, it can achieve heat-resistance of 400° C. or more, optical transmittance of 95% or more, and relative permittivity of 4 or less, preferably 3.3 or less. Those characteristics of light transparency and relative permittivity are not realized by conventional acrylic materials, and hence the cured film of the present invention can be advantageously used in various applications. For example, as described above, it can be adopted as a planarization film of various devices such as flat panel display (FPD), as an interlayer insulating film for low temperature polysilicon, as a buffer coating film for IC chips, and as a transparent protective film.

The present invention will be further explained concretely by use of the following examples and comparative examples. However, those examples and comparative examples by no means restrict the present invention.

EXAMPLE 1

A polysiloxane mixture soluble after prebaked in a 2.38% TMAH aqueous solution was prepared to be a 35% PGMEA solution. To the polysiloxane mixture, a photo-polymerization initiator having sulfonium and borate ions as the cation and anion moieties, respectively, and a silicon-containing compound (pKa=about 4.5; X-12-967C [trademark], manufactured by Shin-Etsu Chemical Co., Ltd.) were added in amounts of 1.2 wt % and 1.7 wt %, respectively, based on the weight of the polysiloxane. Further, a surfactant (KF-53 [trademark], manufactured by Shin-Etsu Chemical Co., Ltd.) was also added in an amount of 0.3 wt % based on the weight of the polysiloxane, to obtain an inorganically developable negative-working photosensitive siloxane composition.

The obtained photosensitive siloxane composition was spin-coated on a silicon wafer, and then prebaked on a hot-plate at 100° C. for 90 seconds to form a coating of 2 μm thickness. The prebaked coating was subjected to exposure at 30 μm/cm$^2$ with g-, h-line exposure apparatus (FX-604 [trademark], manufactured by NIKON corporation, NA=0.1), thereafter baked again on a hot-plate at 100° C. for 90 seconds, subsequently developed by immersion in a 0.8% aqueous solution of potassium hydroxide for 60 seconds, and finally rinsed with pure water for 30 seconds. As a result, a line and space (L/S) pattern and a contact hole (C/H) pattern were formed in 3 μm size without residue left, and hence the composition was verified to be developable with an inorganic developer.

EXAMPLE 2

The procedure of Example 1 was repeated except that the amount of the silicon-containing compound X-12-967C was changed to 0.45 weight part based on 100 weight parts of the polysiloxane.

As a result, a line and space (L/S) pattern and a contact hole (C/H) pattern were formed in 3 μm size without residue left, and hence the composition was verified to be developable with an inorganic developer.

EXAMPLE 3

The procedure of Example 1 was repeated except that the amount of the silicon-containing compound was changed to 3.40 weight parts based on 100 weight parts of the polysiloxane.

As a result, a line and space (L/S) pattern and a contact hole (C/H) pattern were formed in 3 μm size without residue left, and hence the composition was verified to be developable with an inorganic developer.

EXAMPLE 4

The procedure of Example 1 was repeated except that the silicon-containing compound and the amount thereof were changed to X-22-2290AS (pKa=about 4.5; [trademark], manufactured by Shin-Etsu Chemical Co., Ltd.) and 1.20 weight parts based on 100 weight parts of the polysiloxane, respectively.

As a result, a line and space (L/S) pattern and a contact hole (C/H) pattern were formed in 3 μm size without residue left, and hence the composition was verified to be developable with an inorganic developer.

EXAMPLE 5

The procedure of Example 1 was repeated except that the silicon-containing compound and the amount thereof were changed to X-22-1821 (pKa=about 10.0; [trademark], manufactured by Shin-Etsu Chemical Co., Ltd.) and 1.20 weight parts based on 100 weight parts of the polysiloxane, respectively.

As a result, a line and space (L/S) pattern and a contact hole (C/H) pattern were formed in 3 μm size without residue left, and hence the composition was verified to be developable with an inorganic developer.

EXAMPLE 6

The procedure of Example 1 was repeated except that 2,6-di-tert-butyl-4-methylpyridine (manufactured by Tokyo Chemical Industry Co., Ltd.) as an amine additive was added in an amount of 0.1 wt % based on the weight of the polysiloxane.

As a result, a line and space (L/S) pattern and a contact hole (C/H) pattern were formed in 3 μm size without residue left, and hence the composition was verified to be developable with an inorganic developer. In addition, the storage stability was found to be improved although it was slight in degree.

EXAMPLE 7

The procedure of Example 1 was repeated except that the photo-polymerization initiator was changed to a photo acid-generator having iodonium salt and borate as the cation and anion moieties, respectively, in an amount of 2.0 wt % based on the weight of the polysiloxane and also that a sensitizer (ANTHRACURE UVS-1331 [trademark], manufactured by KAWASAKI KASEI CHEMICALS LTD.) was added in an amount of 0.2 wt % based on the weight of the polysiloxane.

As a result, similarly to the examples employing the sulfonium salt, a line and space (L/S) pattern and a contact hole (C/H) pattern were formed in 3 μm size without residue left, and hence the composition was verified to be developable with an inorganic developer.

COMPARATIVE EXAMPLE 1

The procedure of Example 2 was repeated except for not adding the silicon-containing compound, to prepare a negative-working photosensitive siloxane composition.

The prepared composition was spin-coated on a silicon wafer, and then prebaked on a hot-plate at 100° C. for 90 seconds to form a coating of 2 μm thickness. The prebaked coating was subjected to exposure at 45 mJ/cm$^2$ with g-, h-line exposure apparatus (FX-604 [trademark], manufactured by NIKON corporation, NA=0.1), thereafter baked again on a hot-plate at 100° C. for 90 seconds, subsequently developed by immersion in a 0.8% aqueous solution of potassium hydroxide for 60 seconds, and finally rinsed with pure water for 30 seconds. As a result, there was an insoluble layer of about 3500 Å thickness left in the unexposed area and hence it was impossible to obtain a satisfying image by development with an inorganic developer.

COMPARATIVE EXAMPLE 2

The procedure of Example 1 was repeated except that the silicon-containing compound was replaced with maleic acid, which is an organic compound not containing silicon, in an amount of 1.70 weight parts based on 100 weight parts of the polysiloxane.

The prepared composition was spin-coated on a silicon wafer, and then prebaked on a hot-plate at 100° C. for 90 seconds to form a coating of 2 μm thickness. The prebaked coating was subjected to exposure at 45 mJ/cm$^2$ with g-, h-line exposure apparatus (FX-604 [trademark], manufactured by NIKON corporation, NA=0.1), thereafter baked again on a hot-plate at 100° C. for 90 seconds, subsequently developed by immersion in a 0.8% aqueous solution of potassium hydroxide for 60 seconds, and finally rinsed with pure water for 30 seconds. As a result, the formed coating even in the exposed area was completely dissolved away.

COMPARATIVE EXAMPLE 3

The procedure of Example 1 was intended to be repeated except that the silicon-containing compound and the amount thereof were changed to a p-sulfonylphenyl group-containing silane coupling agent (pKa=about 1.9) and 1.70 weight parts based on 100 weight parts of the polysiloxane, respectively. However, the polysiloxane mixture had gradually gelled in the composition since the silicon compound was added therein. Because of that, it was impossible to form a satisfying coating.

COMPARATIVE EXAMPLE 4

The procedure of Example 1 was repeated except that the silicon-containing compound and the amount thereof were changed to a compound having a hydroxyl group at the terminal of a silicone structure (pKa=about 16.0; X-22-160AS [trademark], manufactured by Shin-Etsu Chemical Co., Ltd.) and 1.70 weight parts based on 100 weight parts of the polysiloxane, respectively.

The prepared composition was spin-coated on a silicon wafer, and then prebaked on a hot-plate at 100° C. for 90 seconds to form a coating of 2 μm thickness. The prebaked coating was subjected to exposure at 45 mJ/cm$^2$ with g-, h-line exposure apparatus (FX-604 [trademark], manufactured by NIKON corporation, NA=0.1), thereafter baked again on a hot-plate at 100° C. for 90 seconds, subsequently developed by immersion in a 0.8% aqueous solution of potassium hydroxide for 60 seconds, and finally rinsed with pure water for 30 seconds. As a result, there was an insoluble layer of about 1500 Å thickness left in the unexposed area and hence it was impossible to obtain a satisfying image by development with an inorganic developer.

The invention claimed is:
1. A negative-working photosensitive siloxane composition, comprising
   a polysiloxane,
   a silicon-containing compound having a pKa of 2.0 to 15.7 in water at 25° C. including a carboxyl group, an acid anhydride group, or phenolic hydroxyl group,
   a photo-polymerization initiator, generating an acid or base when exposed to radiation, and
   a solvent, and further wherein said polysiloxane structure is a mixture of polysiloxane 1a and polysiloxane 1b where the siloxane composition has a dissolution rate in 2.38 wt % tetramethylammonium hydroxide and further where la is a polysiloxane, which has a dissolution rate of 3000Å/second or less in a 5 wt % solution of tetramethylammonium hydroxide and lb is a polysiloxane which has a dissolution rate of 150 Å/second or more and further where the weight ratio of polysiloxanes (1a)/(1b) is between 1/99 to 80/20.

2. The negative-working photosensitive siloxane composition according to claim 1, wherein said silicon-containing compound is an acid anhydride group-containing silicone.

3. The negative-working photosensitive siloxane composition according to claim 1, which contains said polymerization initiator in an amount of 0.001 to 10 weight parts based on 100 weight parts of said polysiloxane.

4. The negative-working photosensitive siloxane composition according to claim 1, which contains said silicon-containing compound in an amount of 0.5 to 8.0 weight parts based on 100 weight parts of said polysiloxane.

5. The negative-working photosensitive siloxane composition according to claim 1, which further contains an additive selected from the group consisting of adhesion enhancer, polymerization inhibitor, defoaming agent, surfactant, photosensitizer and stabilizer.

6. A cured film-manufacturing method comprising the steps of: coating on a substrate the negative-working photosensitive siloxane composition according to claim 1, to form a coating; exposing the coating to light;
developing the exposed coating with an inorganic developer; and heating the developed coating.

7. A cured film formed from the negative-working photosensitive siloxane composition according to claim 1.

8. A device comprising the cured film according to claim 7.

9. The negative-working photosensitive siloxane composition according to claim 1, wherein the structure of the polysiloxane is selected from the group consisting of a silicone structure, a silsesquloxane structure, a silica skeleton structure and a mixture thereof.

10. The negative photosensitive siloxane composition according to claim 1 where the weight ratio of polysiloxanes (1a)/(1b) is between 20/80 to 50/50.

11. The negative photosensitive siloxane composition according to claim 1 wherein the mixture of polysiloxanes has a weight average molecular weight of 5000 or less.

12. The negative photosensitive siloxane composition according to claim 11 where the weight average molecular weight is between 1000 and 4000.

* * * * *